United States Patent [19]
Williams et al.

[11] Patent Number: 5,537,453
[45] Date of Patent: Jul. 16, 1996

[54] COAXIAL LASER TARGETING DEVICE FOR USE WITH X-RAY EQUIPMENT

[76] Inventors: Terry N. Williams, 2032 Thorpshire Dr., Raleigh, N.C. 27615; Randal R. Trecha, 1113 N. Shore Dr., Columbia, Mo. 65203

[21] Appl. No.: 344,467

[22] Filed: Nov. 23, 1994

[51] Int. Cl.⁶ ................................................. A61B 6/08
[52] U.S. Cl. .............................. 378/206; 378/205
[58] Field of Search ............................. 378/206, 205, 378/168, 170, 162

[56] References Cited

U.S. PATENT DOCUMENTS

| | | | |
|---|---|---|---|
| 2,217,308 | 10/1940 | Cox | 378/206 |
| 2,486,503 | 11/1949 | Stephens | 378/206 X |
| 3,628,021 | 12/1971 | MacDonald | 378/206 X |
| 5,177,779 | 1/1993 | Cornu et al. | 378/206 |
| 5,212,720 | 5/1993 | Landi et al. | 378/206 |

*Primary Examiner*—David P. Porta
*Attorney, Agent, or Firm*—Rhodes, Coats & Bennett

[57] ABSTRACT

A coaxial laser targeting device is provided for use with x-ray equipment. The device includes an x-ray transparent housing, which encloses a gimbal platform that may be adjustably inclined in any direction. A laser source supplies light through an optical fiber to a lens assembly in the center of the gimbal platform and directs light through a laser emitting aperture in the housing. Three adjustment members arranged in a triangular configuration are used to incline the gimbal platform in any direction relative to the housing to angularly align the laser beam with an x-ray beam emitted by the x-ray equipment so that the beams are coaxial. A visible target created by the laser beam on a patient allows surgeons and the like to accurately perform medical operations without the need to continually operate an x-ray machine.

17 Claims, 2 Drawing Sheets

COAXIAL LASER TARGETING DEVICE FOR USE WITH X-RAY EQUIPMENT

FIELD OF THE INVENTION

The present invention pertains to a laser targeting device for use with x-ray equipment and particularly pertains to a coaxial laser targeting device for use with an x-ray machine having an x-ray emitter on one end of a C-arm and an image intensifier on the other end of the C-arm.

BACKGROUND OF THE INVENTION

Mobile x-ray systems used in most operating rooms are used for a wide range of medical procedures including orthopedic, abdominal, and urological surgery, interventional procedures, vascular interventions, cardiology, neurology, and pulmonology. A mobile x-ray machine generally includes a large counter-balanced C-arm having an x-ray emitter (anode) mounted on one end of the C-arm and an image intensifier fluoroscopy tube on the other end of the C-arm. The C-arm unit is attached to a control unit that houses the necessary generator and electronic controls. The C-arm unit can be articulated in a variety of orbital, height, longitudinal, panning, rotational, and angular axes to properly position the unit for use in a particular medical procedure.

Although prolonged exposure to x-rays is dangerous, in years past, medical procedures were often performed using an x-ray machine that remained on continually during the procedure so that doctors and other medical personnel could see what they were doing. Upon the advent of laser-targeting devices, which aim a laser beam in the path of the x-ray beam, surgery and other operative procedures could be performed without continual x-ray exposure. The laser beam provides a visible target that aids a doctor in maintaining an accurate reference axis without continual operation of the x-ray machine, thereby reducing radiation exposure to doctors and patients. The ability to angularly align a laser beam in precise coaxial alignment with an x-ray beam is of paramount importance because slight discrepancies between the paths of the laser and x-ray beams will result in dangerous mistakes during delicate medical procedures.

Other laser targeting devices claiming to provide; coaxial laser beams have been developed in the past in attempts to aid medical operations under an x-ray machine. However, these prior art devices have at least two serious drawbacks. One drawback is related to the inherent problems with beam drifting that result from flexing of the C-arm, due to its weight, when the C-arm is articulated from one position to another. No prior art device allows an x-ray machine operator to compensate for this inherent beam drift by adjusting the angular alignment of the laser beam. Angular alignment, sometimes referred to as rotational alignment, is parallel, coaxial alignment along the entire length of the laser beam, which is necessary for the laser beam to precisely target a point on a patient under an x-ray machine. Prior art devices only provide for translational adjustment of the laser beam, which involves actually displacing the point source of the laser beam. Translational adjustment may ultimately focus a laser beam on the same remote point that an x-ray beam either focuses on or is emitted from (depending on which direction - the same or opposite, respectively - that the laser beam is emitted relative to the x-ray beam), but coaxial alignment is destroyed when the source of the laser beam is translated relative to the axis of the x-ray beam.

Another drawback of prior laser targeting device designs relates to the location of the focal spot of the anode. This focal spot is the point on the x-ray emitter coinciding with the central axis of x-ray emission. Prior art devices that target a laser by attempting to aim the laser at this focal spot often do so inaccurately because they aim the laser at the geometric center of the emitter, which may not precisely coincide with the central axis of x-ray emission. To accurately target a laser, the laser beam must be aimed at the exact focal spot of the anode, not simply the geometric center of the emitter.

U.S. Pat. No. 5,283,808 to Cramer et al. (hereinafter the '808 patent) discloses an x-ray device having a laser aiming system in an opposed configuration for use with a mobile C-arm x-ray machine. The '808 device comprises two basic components: a laser sight coupled to an x-ray emitter, and a laser housing coupled to an image intensifier.

One inherent problem with the '808 device is that adjustment of the direction of the emitted laser beam is accomplished only by translating the position of the laser beam relative to the image intensifier, which does not enable the device to maintain angular alignment of the laser beam with an x-ray beam. The '808 device reflects a laser beam off of a stationary mirror that does not provide a means for adjusting the direction of the laser beam striking the reflective surface. The '808 device uses only two adjustment screws to move the laser beam source in two orthogonal directions. Therefore, the '808 laser can only be adjusted in only two dimensions and always reflects off of the mirror in a direction perpendicular to the laser housing itself.

Another disadvantage of the '808 device is that its laser sight erroneously positions the laser target reference point in the geometric center of the emitter by providing a laser sight cap that snaps over an end of the emitter and latches in place. The '808 device therefore emits a laser beam that, first, is aimed at the geometric center of the emitter, which might not precisely coincide with the focal spot of the x-ray beam, and second, might not be perfectly coaxial with the x-ray beam, because the '808 device lacks the ability to angularly align the laser beam along the central axis of the x-ray beam.

Other laser targeting devices, such as the device disclosed in U.S. Pat. No. 5,031,203 to Trecha, are similarly flawed in that they have one or both of the aforementioned disadvantages. Until now, no laser targeting device correctly coaxially, angularly aligns the laser beam with the axis of the x-ray beam.

SUMMARY AND OBJECTS OF THE INVENTION

The present invention provides an improved coaxial laser targeting device for use with an x-ray machine having an x-ray emitter on one end of a C-arm and an image intensifier on the other end of the C-arm. The present invention includes an exterior housing composed of a material transparent to x-rays, such as high-temperature plastic, which is mounted to the image intensifier side of the C-arm with a bracket that allows correction of the translational position of the laser device. On the upper surface of the housing is a centrally located laser emitting aperture in the center of a triangle formed by the heads of three adjustment screws. The adjustment screws extend into the housing and are threadably received in corresponding screw holes in a gimbal platform enclosed within the housing. The gimbal platform has a central convex pivot head that has a centrally positioned laser mounting aperture. Embedded in the gimbal platform are x-ray opaque targeting bars, which center on the laser mounting aperture. Each adjustment screw can be manually turned from the exterior of the housing to raise or lower one side of the gimbal platform so that it may be inclined in any direction relative to the central axis of the gimbal platform, which also coincides with the central axis of the x-ray beam. Also contained within the housing is the laser source, which includes a power source, laser circuitry, a laser diode, and a collimating lens assembly. The lens assembly is mounted in the laser mounting aperture in the center of the pivot head. An optical fiber connects the laser diode to the lens assembly for carrying light from the diode to the lens for laser emission in a direction perpendicular to the gimbal platform through the laser emitting aperture in the exterior housing.

The device is operated by aiming the laser beam at a point on the x-ray emitter that coincides with the central axis is of x-ray emission. This point, which is referred to as "the focal spot of the anode," is marked with an x-ray transparent decal in order to visibly indicate the location of the central axis of the x-ray beam. The laser targeting device of the invention can be angularly and translationally adjusted to aim a laser beam in perfect coaxial alignment with an x-ray beam. Translational adjustment initially positions the device in the path of an x-ray beam. Angular adjustment compensates for beam drift that occurs when the C-arm is articulated from one position to another.

It is therefore an object of the present invention to provide a coaxial laser targeting device that precisely angularly aligns a laser beam with an x-ray beam.

It is another object of the present invention to provide a coaxial laser targeting device having a gimbal platform that can be inclined in any direction relative to a housing.

It is still another object of the present invention to provide a coaxial laser targeting device that accurately aims a laser beam at the focal spot of the anode of an x-ray machine.

It is yet another object of the present invention to provide a coaxial laser targeting device that uses an optical fiber to transmit light from a laser source to a collimating lens assembly in the center of the gimbal platform.

It is another object of the invention to provide a coaxial laser targeting device for use with all existing C-arm type x-ray machines.

It is still another object of the present invention to provide a method of aiming a laser beam coaxially with an x-ray beam to provide a visible target to aid medical procedures and thereby eliminate the necessity of leaving the x-ray machine continuously on.

Other objects and advantages of the present invention will become apparent and obvious from a study of the following description and tile accompanying drawings which are merely illustrative of such invention.

DETAILED DESCRIPTION OF THE INVENTION

The coaxial laser targeting device of the invention provides a unique design that overcomes the disadvantages and deficiencies of prior art designs. The present invention is the first such device that allows for precise adjustment of the angular alignment of a laser beam with an x-ray beam. This object is achieved by mounting a laser source on a gimbal platform that can be inclined in any direction. The laser beam emitted by a laser source is aimed at precisely the point at which the x-ray beam is emitted by an x-ray machine's anode. The present invention can conveniently be used with all commonly available mobile C-arm type x-ray machines, which have an x-ray emitter (anode) on one end of the C-arm and an image intensifier on the other end of the C-arm.

Figure 1:
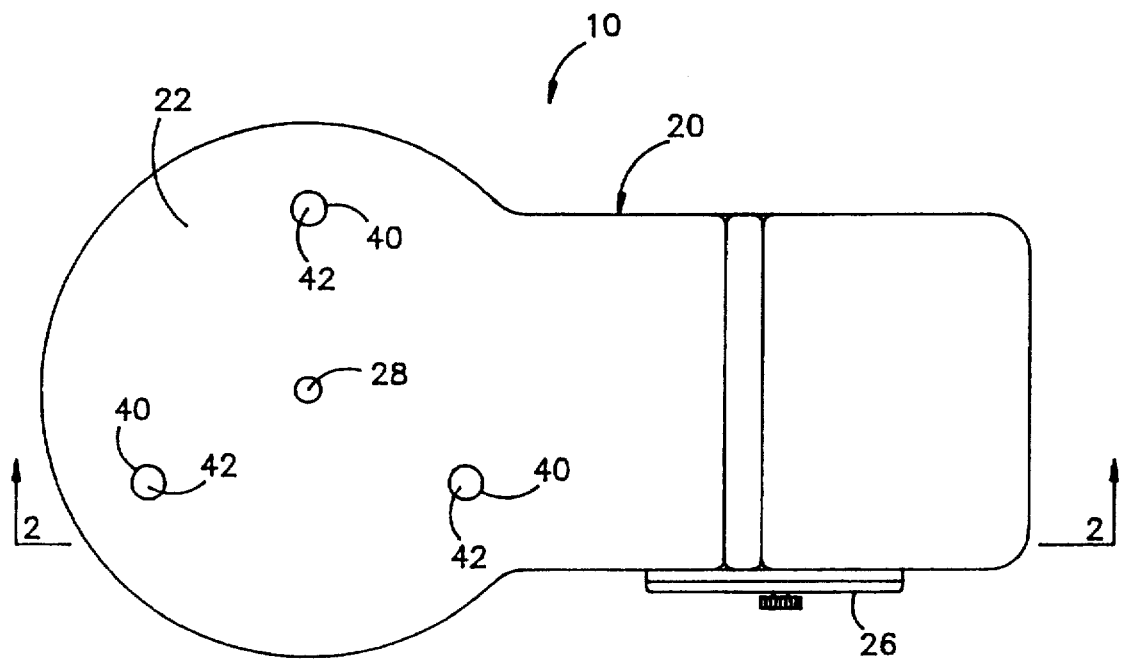
FIG. 1 is a top view of the coaxial laser targeting device of the invention.

A top view of the coaxial laser targeting device 10 is shown in FIG. 1. The device 10 includes a protective housing 20 composed of a material that is transparent to x-rays and durable enough to withstand repeated sterilization, as is necessary for use in the medical field. The housing includes a top half 22 and a bottom half 23 which are secured together by any suitable means, such as by screws. The housing top half 22 includes a laser emitting aperture 28. Three adjustment members 40 are equally spaced around the aperture 28. In the disclosed embodiment, the adjustment members 40 are screws. The heads 42 of the screws are disposed exteriorly of the housing 20 and can be manually rotated. The purpose of the adjustment members 40 will be explained below. Also seen on the housing 20 is a bracket 26, which is used to attach the coaxial laser targeting device 10 to the image intensifier side of a C-arm type x-ray machine. The bracket 26 is translationally adjustable so that the device 10 can be initially set in proper alignment with the x-ray beam. The bracket 26 also allows the laser targeting device 10 to be easily and quickly removed from an x-ray machine for cleaning and sterilization between medical operations.

Figure 2:
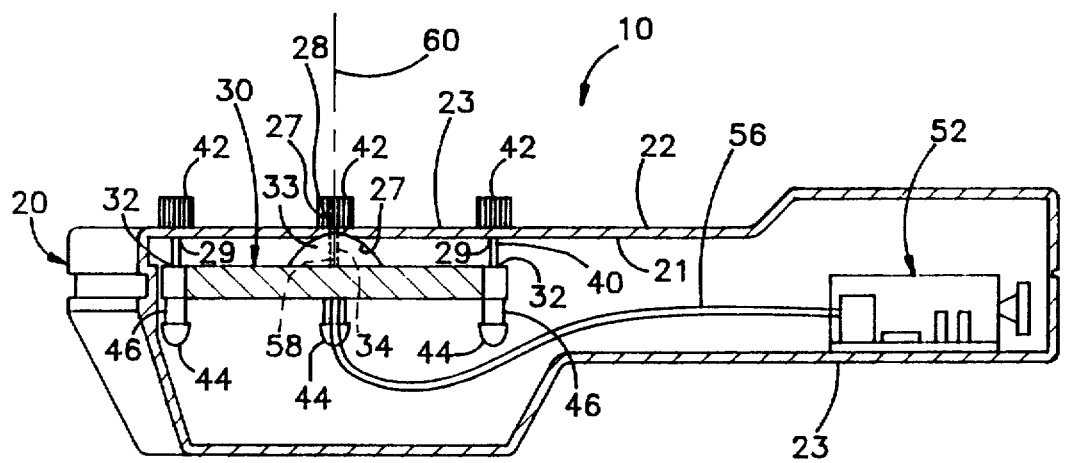
FIG. 2 is a fragmentary side elevational view of the coaxial laser targeting device revealing gimbal platform and the laser source.

FIG. 2 shows a cut-away side view of the coaxial laser targeting device 10. Here can be seen the adjustment members 40, which in this embodiment are threaded screws, extending through holes 29 in the top half 22 of the housing. The adjustment members engage corresponding screw holes 32 in the gimbal platform 30. On the bottom end of each threaded adjustment screw 40 is a spacer 46 and an end cap 44. Turning of any one of the adjustment screws 40 causes the gimbal platform 30 to be pivoted relative to its central axis. Three adjustment screws 40 are provided in this embodiment so that the gimbal platform 30 can be pointed in any direction by selectively turning one or more adjustment screws 40. As can be seen in FIG. 2, each threaded adjustment screw hole 32 in the gimbal platform 30 is in axial alignment with a corresponding adjustment screw aperture 29 in the housing top half 22.

At the center of the gimbal platform 30 is a convex, dome-shaped pivot head 33 that includes a centrally positioned laser mounting aperture 34. The laser mounting aperture 34 is directly below and aligned with the laser emitting aperture 28 in the housing top half 22. The convex pivot head 33 mates with a shallow concave well 27 on the underside 21 of the housing top half 22, the laser emitting aperture 28 being centrally disposed in the concave well 27. The pivot head 33 functions as a fulcrum about which the gimbal platform 30 pivots.

FIG. 2 also shows components of the laser source, including an optical fiber 56 that carries light from laser circuitry 52 to a collimating lens assembly 58, which is mounted in the laser mounting aperture 34. When the laser targeting device 10 is activated, a laser beam is emitted from the lens assembly 58, the central axis 60 of the laser beam being perpendicular to the gimbal platform 30. It should be appreciated that the central axis 60 of the laser beam is not necessarily perpendicular to the upper surface 23 of the housing top half 22. This configuration of the convex pivot head 33 and concave well 27 positions the lens assembly 58 nearly at the upper surface 23 to prevent the laser beam from being deflected or obstructed as it passes through the laser emitting aperture 28.

Figure 3:
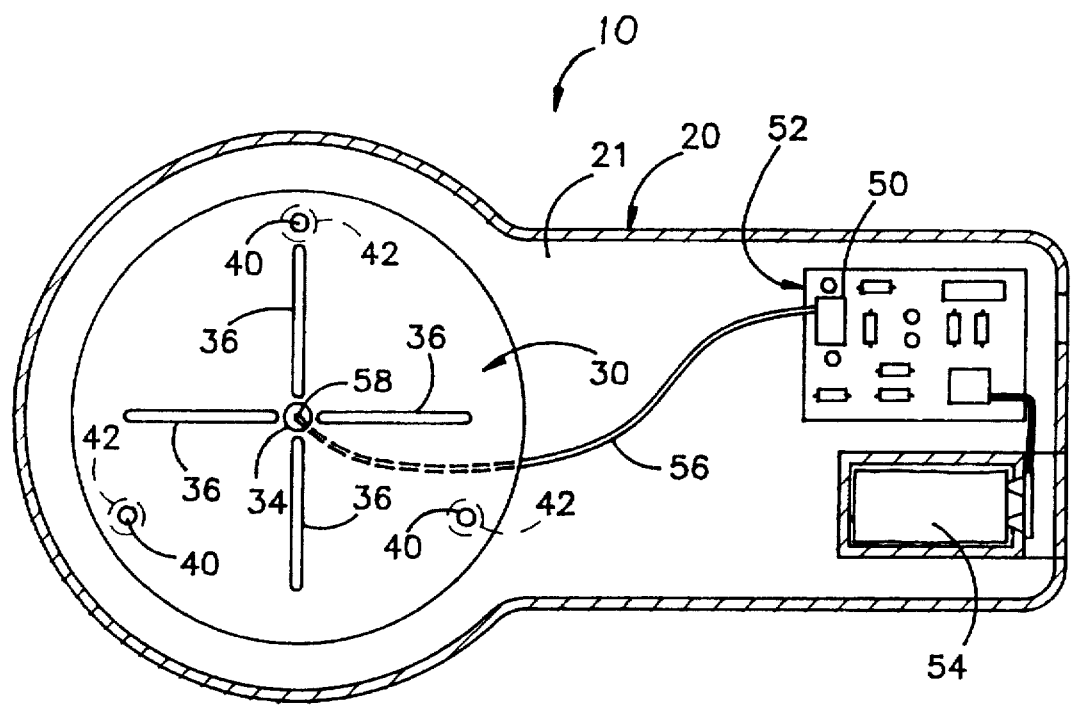
FIG. 3 is a bottom view of the interior of the coaxial laser targeting device as seen with the housing bottom half removed.

FIG. 3 better illustrates the laser circuitry 52 within the housing 20. FIG. 3 shows the coaxial laser targeting device 10 with the housing bottom half 24 removed to show the internal components. A power source such as a battery 54 powers the laser circuitry 52, which includes a laser diode 50 for emitting light. As can be seen in this bottom view of the components, the gimbal platform 30 includes targeting cross bars 36, which extend outwardly from the laser mounting aperture 34. The optical fiber 56 curves up into the bottom of the gimbal platform 30 to supply light to the lens assembly 58 in the center of the gimbal platform 30. The targeting cross bars 36 are made of a x-ray opaque material such as lead and are embedded in the gimbal platform 30.

Figure 4:
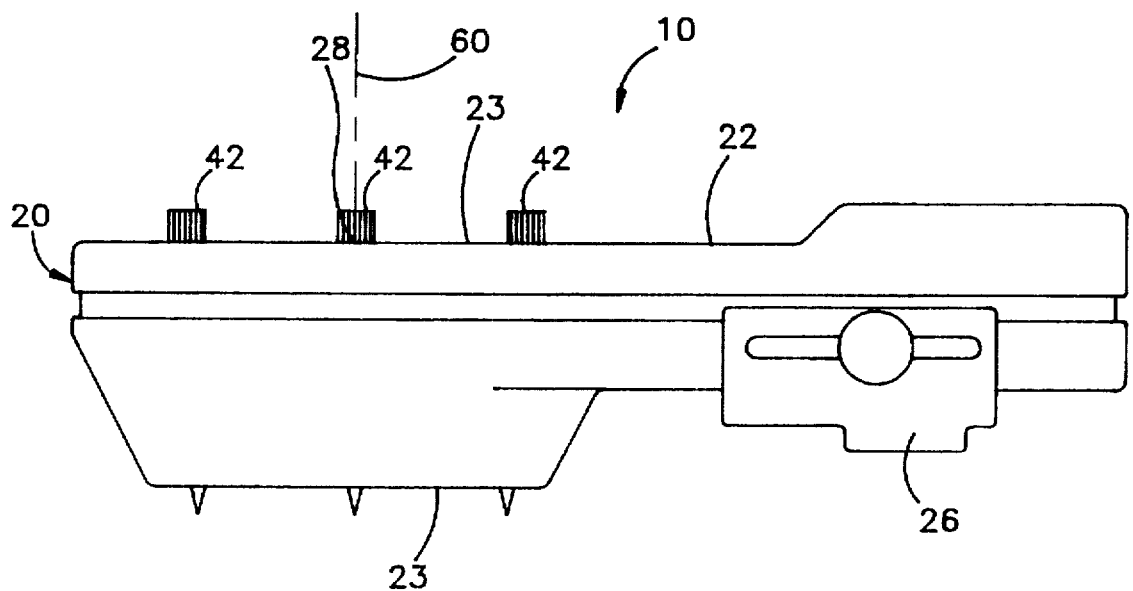
FIG. 4 is a side elevational view of the coaxial laser targeting device.

FIG. 4 shows a side elevational view of the coaxial laser targeting device 10. The bracket 26 is shown on a side of the housing 20 and can be moved back and forth along the housing 20 to adjust the translational position of the targeting device 10 on the image intensifier of an x-ray machine. Also seen in FIG. 4 are the adjustment screw heads 42 exterior to the housing top half 22 for easy access by an x-ray technician or other operator of the x-ray machine.

The present invention also includes a method of aiming a laser beam coaxially with an x-ray beam emitted by an x-ray machine to provide a visible target to aid medical procedures. The coaxial laser targeting device 10 is designed to be used with an x-ray machine with a mobile C-arm having an x-ray emitter (anode) at one end and an image intensifier at the other end. The emitter has a central axis of emission designated as the focal spot of the anode. A physicist or x-ray technician first locates this point of emission on the emitter and accurately labels it with a target decal or the like in order to visibly indicate the central axis of the x-ray beam. If this is not accomplished, significant inaccuracies will occur when the coaxial laser targeting device 10 is used. Likewise, the geometric center of the emitter may not be exactly the same point as the focal spot of the anode. This discrepancy causes prior art laser targeting devices to have inherent inaccuracies in their operation.

The next step is to position the laser targeting device 10 on the image intensifier side of the C-arm. Proper translational positioning is accomplished by locating the geometric center of the image intensifier and positioning the laser mounting aperture 34 to correspond to this point by translating the targeting device 10 on the adjustable bracket 26. This can be achieved by activating the x-ray machine and moving the laser targeting device 10 until the targeting cross bars 36 embedded in the gimbal platform 30 are centered in the x-ray beam.

Next, the x-ray machine is turned off and the laser circuitry 52 is activated to emit a laser beam perpendicular to the gimbal platform 30 through the laser emitting aperture 28 in the housing top half 22. The laser beam is then directed to aim at the target decal, which marks the focal spot of the anode, by turning one or more of the adjustment screws 40.

This adjustment and alignment should be checked every time the C-arm is moved because flexing of the C-arm occurs upon movement due to its weight. By selectively adjusting the threaded adjustment screws 40, the gimbal platform 30 can be inclined in any direction relative to the housing 20 so that the central axis 60 of the laser beam is in exact coaxial alignment with the x-ray beam.

This method of aiming a laser beam with the coaxial laser targeting device 10 of the invention is superior to methods of aiming prior art lasers. With prior art devices, the inherent flexing of the C-arm can result in the laser beam being emitted from a point that is not in the axis of the x-ray beam. While the prior art devices may provide methods of aiming the laser beam at a central point on the anode, they do not ensure angular, coaxial alignment of the beams.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. A laser targeting device for emitting a laser beam in coaxial alignment with the central axis of an x-ray beam, said laser targeting device comprising:

a) a laser source for emitting a laser beam;
   b) a laser mount for mounting the laser source to an x-ray machine such that the laser source is positioned along the central axis of the x-ray beam, said laser mount including a gimbal platform having a fulcrum on which said gimbal platform rotates; and
   c) an adjustment member engaged with the gimbal platform and operative to pivot said gimbal platform about said fulcrum to adjust the angle of the laser beam with respect to the central axis of said x-ray beam to compensate for drift of the x-ray beam.

2. The laser targeting device of claim 1 wherein said adjustment member includes means for tilting said gimbal platform relative to a central axis.

3. The laser targeting device of claim 1 wherein said fulcrum is positioned at the center of said gimbal platform to permit rotation of the gimbal platform in any direction relative to said central axis.

4. The laser targeting device of claim 2 wherein said adjustment member comprises at least one adjustment screw.

5. The laser targeting device of claim 4 wherein said adjustment screw is threadably engaged in a corresponding screw hole in the gimbal platform.

6. The laser targeting device of claim 5 including at least three adjustment screws equally spaced about the center of the gimbal platform, each said adjustment screw being threadably engaged in a corresponding screw hole in the gimbal platform.

7. A method of aiming a laser beam coaxially with an x-ray beam emitted by an x-ray machine, thereby providing a visible target to aid medical procedures, comprising the steps of:

a) mounting a laser beam source on an angularly adjustable gimbal platform;
   b) securing the gimbal platform to said x-ray machine such that the laser source is positioned along the central axis of the x-ray beam;
   c) adjusting the angle of the laser beam relative to the central axis of the x-ray beam by inclining the adjustable gimbal platform on a fulcrum in a direction opposite to angular drift of the laser beam.

8. A laser targeting device for use with x-ray equipment, comprising:
   a) an x-ray transparent housing including a laser emitting aperture;
   b) a gimbal platform enclosed within the housing, said gimbal platform including a fulcrum on which said gimbal platform pivots;
   c) a laser source mounted on the gimbal platform for emitting a laser beam through the laser emitting aperture in the housing; and
   d) adjustment means for pivots the gimbal platform in any direction relative to the central axis of the x-ray beam to compensate for drift of the laser beam with respect to the central axis of the x-ray beam.

9. The laser targeting device of claim 8, wherein the adjustment means comprises at least three adjustment screws that engage the gimbal platform at equally spaced locations relative to the center of the gimbal platform.

10. The laser targeting device of claim 9, wherein each adjustment screw is threadably engaged in a corresponding screw hole in the gimbal platform.

11. The laser targeting device of claim 8, wherein the laser source comprises a laser diode, a collimating lens assembly, and an optical fiber extending between the laser diode and the lens assembly.

12. The laser targeting device of claim 11, wherein the laser beam is emitted along the central axis of the gimbal platform such that the laser beam is perpendicular to the gimbal platform.

13. The laser targeting device of claim 12, wherein the gimbal platform includes a plurality of x-ray opaque targeting bars embedded in the gimbal platform and extending outwardly from the center of the gimbal platform.

14. The laser targeting device of claim 8, further comprising a bracket attached to the housing to adjustably mount the coaxial laser targeting device to an x-ray machine.

15. A laser targeting device for use with x-ray equipment, comprising:
   a) an x-ray transparent housing;
   b) a gimbal platform disposed in said housing, said gimbal platform including a fulcrum on which said gimbal platform is pivoted;
   c) a laser source for emitting a laser beam in alignment with an x-ray beam, including:
      i) a laser diode within said housing,
      ii) a collimating lens mounted on said gimbal platform, and
      iii) an optical fiber for transmitting light from the laser diode to the collimating lens on said gimbal platform; and
   d) adjustment means for inclining said gimbal platform in any direction relative to the central axis of the x-ray beam to compensate for drift of the laser beam with respect to the central axis of the x-ray beam.

16. The laser targeting device of claim 15, wherein said housing includes a laser emitting aperture, and wherein the collimating lens is disposed in alignment with the laser emitting aperture.

17. The laser targeting device of claim 15, wherein the collimating lens is mounted in the fulcrum.

* * * * *